United States Patent [19]

Michaelis et al.

[11] Patent Number: 5,434,067
[45] Date of Patent: Jul. 18, 1995

[54] PROCESS FOR THE PRODUCTION AND RENATURATION OF RECOMBINANT, BIOLOGICALLY ACTIVE, EUKARYOTIC ALKALINE PHOSPHATASE

[75] Inventors: Uwe Michaelis; Rainer Rudolph, both of Weilheim; Michael Jarsch, Bad Heilbrunn; Erhard Kopetzki, Penzberg; Helmut Burtscher, Habach; Gëther Schumacher, Bernried, all of Germany

[73] Assignee: Boehringer Mannheim GmbH, Mannheim-Waldhof, Germany

[21] Appl. No.: 100,124

[22] Filed: Jul. 30, 1993

[30] Foreign Application Priority Data

Jul. 31, 1992 [DE] Germany ............... 42 25 427.2

[51] Int. Cl.$^6$ ............... C12N 9/12; C12N 15/54; C12N 15/70; C07K 1/36
[52] U.S. Cl. ............... 435/196; 435/69.1; 435/320.1; 530/412
[58] Field of Search ............ 435/69.1, 196, 804, 435/814, 849, 252.33, 320.1; 530/412

[56] References Cited

U.S. PATENT DOCUMENTS 4,659,666 4/1987 May et al. ............... 435/196

FOREIGN PATENT DOCUMENTS 0151320 8/1985 European Pat. Off. .
298424 2/1992 German Dem. Rep. .
1082811 3/1984 U.S.S.R. .

OTHER PUBLICATIONS

Fernly, "Mammalian Alkaline Phosphatases", pp. 422–427 in *The Enzymes* vol. IV, edited by Boyer, (1971).
Low et al., *Biochem. J.* 241:615–619 (1987).
Bingham et al., "Purification and Properties of Alkaline Phosphatase . . ." *J. Dairy Sci.* 75: 3394–3401 (Dec. 1992).
Besman et al. "Isozymes of Bovine Intestinal Alkaline Phosphatase" J. Biol. Chem. 260:11190–11193 (Sep. 1985).
Holyaerts et al., *Biochem. J.* 286:23–30 (Aug. 1992).
Hermann, R., EPO Applied Technology Series, vol. 12: Protein Folding EPO, The Hauge, The Netherlands (1993) pp. 1, 44–45, 62–65, 108–110.
Torchilin, V. P., Enzyme Microb. Technol. vol. 1, pp. 74–81 (1979).
Cleland, J. L., et al. Biotechnology, vol. 8, pp. 1274–1278 (1990).
Timasheff, S. N., et al., Biophysic of Water, (Franks & Marthias Eds.) Wiley & Sons pp. 48–49 (1982).
Chemical Abstract, Enzymes vol. 69, p. 3871, abstract No. 41426m (1968).
Chemical Abstract, vol. 91, p. 624 abstract No. 89776g (1979).

*Primary Examiner*—Stephen G. Walsh
*Attorney, Agent, or Firm*—Felfe & Lynch

[57] ABSTRACT

In a process for the production of recombinant, biologically active, eukaryotic alkaline phosphatase a DNA sequence coding for a eukaryotic alkaline phosphatase is expressed in a prokaryotic host cell and the expression product is obtained in an active form by cell lysis, solubilization under denaturing conditions and subsequent renaturation. In this process the renaturation step is carried out in the presence of one or several stabilizing agents.

26 Claims, No Drawings

PROCESS FOR THE PRODUCTION AND RENATURATION OF RECOMBINANT, BIOLOGICALLY ACTIVE, EUKARYOTIC ALKALINE PHOSPHATASE

The present invention concerns a process for the production of biologically active, recombinant, eukaryotic alkaline phosphatase by expression in prokaryotes.

Alkaline phosphatases are metalloenzymes which are wide-spread in nature and catalyze hydrolysis of phosphate ester bonds at alkaline pH values. They have been described for a long time for example as tumour-associated proteins (Fröhlander, N. S. Millan, J. L. (1991), In vivo 5, 483–488; McComb et al. (1979), Alkaline Phosphatases, Plenum Press). However, their actual function is still largely unknown. Alkaline phosphatases have many applications in biological research as well as in genetic engineering and in medical diagnosis, e.g. as important marker enzymes for enzyme-immunoassays. Eukaryotic alkaline phosphatases usually have a higher specific activity in comparison to the described prokaryotic enzymes (McComb et al. (1979), Alkaline Phosphatases, Plenum Press). Moreover the activities of alkaline phosphatases in mammals are tissue-specific and occur for example in the intestinal epithelium (intestine), in the placenta, in the kidney, the bones and in the liver (Meyer-Sabellek et al. (1988), Journal of Chromatography 429, 419–444).

A cheap recombinant production of eukaryotic alkaline phosphatases of constant quality is therefore of great interest also with regard to reducing the risk of infection (HIV, BSE) during their isolation from tissues and equally because of the problem of obtaining heterogeneous enzyme mixtures in the isolation from tissues.

Relatively insoluble, biologically inactive protein aggregates (inclusion bodies) are often formed during the heterologous expression of eukaryotic proteins in prokaryotes. In most cases these can be converted back into their biologically active form using well known methods (Jaenicke, R. (1979) FEBS Letters, Vol. 52, 187–198; Rudolph R. (1990), Modern Methods in Protein and Nucleic Acid Research, 149–171). In this process, the proteins present in the inclusion bodies are solubilized under reducing conditions by addition of strong denaturing agents such as e.g. urea, guanidine hydrochloride or by addition of strongly acidic agents, such as glycine/phosphoric acid mixtures, and subsequently renatured.

Various processes are described in the state of the art for the renaturation of denatured proteins (e.g. DE 35 37 708 A1, DE 38 35 350 A1, EP-A 0 241 022).

For example, a process is disclosed in EP-A 0 114 506 for the purification and reactivation of heterologously expressed proteins. In this process, the proteins present in inclusion bodies are dissolved with a strong denaturing agent and subsequently transferred into a weaker denaturing solvent where they are subjected to oxidizing conditions for the formation of disulfide bridges. Alternatively, before transfer into a weaker denaturing solvent, the proteins are sulfonated and subsequently renatured in the presence of the weaker denaturing solvent with formation of S—S bonds by reaction with a sulfhydryl reagent in its reduced and oxidized form. Although a series of eukaryotic alkaline phosphatases have been cloned (Kam et al. (1985), Proc. Natl. Acad. Sci., USA 82, 8715–8719; Millan J. L. (1986), J. Biol. Chem. 261, 3112–3115; Henthorn et al. (1987), Proc. Natl. Acad. Sci., USA 84, 1234–1238; Hsu, H. H. T. & Anderson, H. C. (1989), Int. J. Biochem. 21, 847–851; Millan, J. L. (1988), Anticancer Research 8, 995–1004; Harris, H. (1989), Clinica Chimica Acta 186, 133–150; Smith, A. F. (1989), Clin. Chem. Enzyme. Comms 2, 1–22; Millan J. L., (1990), Isozymes: Structure, Function and Use in Biology and Medicine, 453–475, Wiley-Liss Inc.) it has previously not been possible to express the enzyme in prokaryotes with successful renaturation into its biologically active form.

Therefore the object of the present invention is to provide a process for the renaturation of eukaryotic alkaline phosphatases after expression in prokaryotes.

This object is achieved according to the present invention by expressing a DNA sequence coding for a eukaryotic alkaline phosphatase in a prokaryotic host cell and isolating the expression product in an active form by cell lysis, solubilizing the expression product under denaturing conditions, and subsequently renaturating the expression product wherein the renaturation step is carried out in the presence of one or several stabilizing agents.

Surprisingly, the process according to the present invention enables alkaline phosphatases to be obtained in a biologically active form after expression in prokaryotes, whereby it is particularly remarkable that in contrast to previously known methods, the renaturation of heterologously expressed alkaline phosphatases can be successfully carried out in the presence of one or several stabilizing agents. The process is particularly preferably carried out using placental alkaline phosphatase. However, other phosphatases such as phosphatase from calf intestine, etc., have also proven to be suitable.

Agents which can be used as stabilizing agents within the scope of the present invention are those which stabilize proteins in solution such as e.g., synthetic polymers, monosaccharides, oligosaccharides and polysaccharides, polyalcohols, salts, etc. (Gupta, M. N. (1991), Biotechnology and Applied Biochemistry 14, 1–11; Gray, C. J. (1988), Biocatalysis 1, 187–196; Busby, T. F. & Ingham, K. C. (1984), Biochem. Biophys., Acta 799, 483–488). In this connection, sulfate salts, carbohydrates or polyalcohols either alone or in combination with one another are preferred according to the present invention.

In a preferred embodiment of the process according to the present invention, sodium sulfate or potassium sulfate or ammonium sulfate or mixtures of these are used as stabilizing agents. In this case, sodium sulfate is preferably used in an amount of 0.3 to 1 mol/l, preferably in an amount of 0.3 to 0.6 mol/l. Potassium sulfate is preferably used in an amount of 0.1 to 0.6 mol/l, particularly preferably in an amount of 0.1 to 0.45 mol/l. Ammonium sulfate is preferably used in an amount of 0.3 to 1 mol/l.

In a further preferred embodiment, carbohydrates are used as stabilizing agents. In this case, carbohydrates are preferably used in an amount of 5 to 50% weight/volume relative to the volume of the renaturation mixture. Pentoses such as e.g. arabinose, hexoses such as e.g. galactose, glucose or fructose, various disaccharides such as e.g. lactose, maltose or sucrose or mixtures of pentoses, hexoses or/and disaccharides are preferably used as carbohydrates.

In a further preferred embodiment, various polyalcohols in an amount of 5 to 50% weight/volume relative to the volume of the renaturing mixture, such as e.g. sorbitol, glycerol, erythritol, inositol, ethylene glycol or mixtures thereof can also be used.

In a particularly preferred embodiment of the present invention, it is possible to use mixtures of carbohydrates, polyalcohols or/and sulfate salts to renature eukaryotic alkaline phosphatases. Surprisingly, a synergistic effect is observed in this case which results in an increase in the efficiency of the renaturation and which exceeds the additive value of the individual components.

In describing the standard renaturation buffers which are used in the examples to which the respective stabilizing agents are added according to the present invention, it is, however, not intended to exclude buffer solutions with other compositions that may be suitable for use in the process according to the present invention.

The heterologous expression of a cloned DNA sequence in a prokaryotic host cell is known from the state of the art. The introduction of the DNA sequence into the host cell can, for example, be carried out by transformation with a vector which contains at least one copy of the DNA sequence. Extrachromosomal vectors (e.g. plasmids) as well as integration vectors (e.g. lambda vectors) are suitable for this whereby plasmids are, however, preferred. The prokaryotic host cell is preferably a gram-negative host cell, particularly preferably an E. coli cell. With regard to the various techniques for cloning genes and transforming host cells, reference is made to Sambrook et al. (Molecular Cloning. A Laboratory Manual (1989), Cold Spring Harbor Laboratory Press).

The culture of the transformed host cell in the process according to the present invention to obtain recombinant biologically active, eukaryotic alkaline phosphatase takes place under conditions which are favourable for the expression of a DNA sequence. In a preferred embodiment, the DNA sequence is operatively linked to a regulatable promoter that can be induced by addition of an inducer or by increasing the temperature. Furthermore, it may be preferable that, in addition to the vector containing the phosphatase gene, further auxiliary vectors that improve the expression are present in the host cell (e.g. pUBS 500). A particularly preferred vector for the production of recombinant placental alkaline phosphatase is the plasmid pPLAP (DSM 7094).

Cell lysis after the expression can be carried out by all the usual methods for this, e.g., by means of ultrasound, high pressure dispersion or lysozyme. It is preferably carried out in a buffer solution which is suitable for setting a neutral to weakly acidic pH value such as, e.g., 0.1 mol/l Tris/HCl. The lysed cells are then separated into a soluble and an insoluble fraction, preferably by means of centrifugation or filtration. Alkaline phosphatase is then generally located in the insoluble fraction or the pellet in the form of inclusion bodies. After washing the pellet with agents which do not interfere with the alkaline phosphatase proteins present in the form of inclusion bodies, but which dissolve impurities such as foreign proteins as far as possible, the pellet is subjected to a solubilization procedure (solubilization, reduction) according to known methods. The solubilization is preferably carried out in an alkaline pH range, in particular, at pH 8 in the presence of reducing agents and high concentrations of denaturing agents, preferably 8 mol/l urea. The solubilization can, for example, be carried out at room temperature for a period of at least 2 hours. The pH value is preferably adjusted to values of 3 to 4 by addition of HCl after completion of the solubilization and the insoluble substances are separated by known methods in a subsequent purification step. The reducing agent which is used is subsequently removed preferably by means of dialysis against the denaturing agent.

A feature of the process according to the present invention is that the renaturation step is carried out in the presence of one or several of the aforementioned stabilizing agents. In this process, it is preferred that the renaturation be carried out essentially in the absence ($\leq 50$ mmol/l) of chaotropic, i.e. denaturing, agents such as guanidinium hydrochloride or urea. However, it was found that even with higher concentrations of chaotropic agents that however, do not have a denaturing effect (e.g. up to 800 mmol/l urea), it is possible to renature alkaline phosphatase according to the present invention when the aforementioned stabilizing agents are present at the same time, although a lower renaturation efficiency is observed.

The renaturation step can be carried out according to all known and common procedures provided that one or several stabilizing agents are present. Thus, in the process according to the present invention it is possible to use the pulse renaturation method known from EP-A 0 241 022 and at the same time use either the process disclosed in DE 3 835 350 A1 via the mixed disulphide or a direct reaction with a disulphide and a mercaptan. In doing so it may, however, be expedient to carry out individual steps or all steps in the procedure taking into consideration the process design elucidated here.

In this process, the renaturation is preferably carried out at 10° to 40° C., particularly preferably at 20° C. A preferably used renaturation buffer contains Tris-HCl buffer in an amount of 0.1 to 0.3 mol/l and has a pH value of 6 to 10, preferably of 7 to 9, and in the most preferable embodiment a pH value of about 8 and contains magnesium ions and zinc ions in amounts of 0.1 to 200 mmol/l (magnesium chloride) and 0.01 to 0.5 mmol/l (zinc chloride). The amount of magnesium ions in the renaturation mixture is preferably 10 mmol/l and that of zinc ions 0.1 mmol/l. The renaturation mixture additionally preferably contains sulfhydryl reagents at a concentration of preferably 0.1 to 10 mmol/l, particularly preferably of 2 to 5 mmol/l. A preferred sulfhydryl reagent in the process according to the present invention is glutathione in its reduced or/and oxidized form.

The invention in addition concerns a recombinant eukaryotic, non-glycosylated alkaline phosphatase which is obtainable by the process according to the present invention. The specific activity of the recombinant alkaline phosphatase is about 1000 U/mg after a first crude purification. The specific activity can be increased by a factor of about 2–3 by further purification steps.

The invention is further elucidated by the following examples in conjunction with tables 1 to 11 and the sequence protocols SEQ ID NO. 1 to 3.

Table 1 shows the dependence of renaturation efficiency on $Na_2SO_4$ concentration, Table 2 shows the dependence of renaturation efficiency on $K_2SO_4$ or $(NH_4)_2SO_4$ concentration, Table 3 shows the dependence of renaturation efficiency on galactose, glucose and fructose, lactose, maltose, sucrose, sorbitol, glycerol, ethylene glycol and arabinose, Table 4 shows the effect of glycerol and $K_2SO_4$ on the renaturation efficiency, Table 5 shows the dependence of renaturation efficiency on the pH value, Table 6 show the dependence of renaturation efficiency on the GSH concentration, Table 7 shows the dependence of renaturation efficiency on the GSSG concentration, Table 8 shows the dependence of renaturation efficiency on the GSH and GSSG concentration at an equimolar GSH/GSSG ratio, Table 9 shows the dependence of renaturation efficiency on the $ZnCl_2$ concentration, Table 10 shows the dependence of renaturation efficiency on the $MgCl_2$ concentration and Table 11 shows the influence of temperature on the renaturation efficiency.

SEQ ID NO:1 shows primer (1) used to amplify the PLAP structural gene,

SEQ ID NO.2 shows primer (2) used to amplify the PLAP structural gene,

SEQ ID NO.3 shows primer (3) used to amplify the PLAP structural gene.

The microorganism E. coli RM 82 used in the examples was deposited on the 13th Jul. 1989 at the "Deutsche Sammlung für Mikroorganismen und Zellkulturen GmbH (DSM)", Mascheroder Weg 1b, D-3300 Braunschweig under the depositary number DSM 5445. The plasmid mixture pPLAP/pUBS500 was deposited on the 3rd Jun. 1992 under the depositary number DSM 7094 at the same depositary institution.

Abbreviations used:
AP: alkaline phosphatase
DTE: dithioerythritol
GSH: reduced glutathione
GSSG: oxidized glutathione
IBs: inclusion bodies
mucosa-AP: alkaline phosphatase from calf intestine
PLAP: placental alkaline phosphatase
RT: room temperature
ON: overnight

EXAMPLE 1

Construction of the expression plasmid pPLAP 1.1 Subcloning of the PLAP gene

The PLAP gene was isolated from the lambda-gt11-PLAP clone (Millan, J. L. (1986), J. Biol. Chem. 261, 3112-3115) as approximately 2 kbp long EcoRI/KpnI fragment and ligated into the approximately 2.85 kbp long pGEM3 vector from the Promega company which had been digested with EcoRI and KpnI.

1.2 Construction of the E. coli expression vector pD-NX

Plasmid pD-NX is a derivative of plasmid pQE-6 (pDS56/RBSII, NcoI) from the Diagen company (Düsseldorf) from which the promoter-free chloramphenicolacetyltransferase gene (CAT) had been removed.

For this plasmid pDS56/RBSII,NcoI was digested with the restriction endonucleases NheI and XbaI, the approximately 2.6 kbp long NheI/XbaI vector fragment was isolated and the compatible ends of the NheI and XbaI cleavage site were linked by means of ligation (construction: pD-NX).

1.3 Construction of the E. coli expression plasmid pPLAP

The PLAP structural gene was amplified from base pair position 105-1556 (numbering according to the publication by Millan, 1986) in 2 partial reactions by means of the PCR technique (Mullis and Faloona (1987), Meth. Enzymol. 155, 335-350). The PCR primers were selected so that the PLAP structural gene is flanked by suitable restriction endonuclease cleavage sites after the PCR reaction (5' end: BspHI and 3' end: HindIII). Afterwards the PLAP structural gene was assembled from the two PCR fragments in a three fragment ligation and inserted into the E. coli vector pD-NX.

The following primer pair (1) and (2) (see SEQ ID NO. 1 and SEQ ID NO. 2) and plasmid pGEM3-PLAP as template DNA were used to amplify the N-terminal PLAP structural gene.

Primer (1): 5'-GCGCGTCGACTCATGATCATC-CCAGTTGAGGAG-3'(SEQ ID NO.1) BspHI

Primer (2): 5'-CATCCCATCGCCCAGG-3'(SEQ ID NO.2)

The following primer pair (see SEQ ID NO. 1 and SEQ ID NO. 3) and plasmid pGEM3-PLAP as template DNA were used to amplify the remaining PLAP structural gene.

Primer (1): 5'-GCGCGTCGACTCATGATCATC-CCAGTTGAGGAG-3'(SEQ ID NO.1)

Primer (3): 5'-CAATTAAGCTTTTAT-CAGTCGGTGGTGCCG-3'(SEQ ID NO.3)

The approximately 150 bp long PCR product of the first reaction was recleaved with BspHI and PstI and the approximately 90 bp long BspHII/PstI fragment was isolated. The approximately 1.48 kbp long PCR product of the second reaction was digested with PstI and HindIII and the approximately 1.39 kbp long PstI/-HindIII fragment was isolated. Afterwards the PCR fragments were ligated into the ca- 2.55 kbp long NcoI/HindIII-pD-NX vector fragment (three fragment ligation). The desired plasmid pPLAP was identified by restriction mapping and partially sequenced (cloning junctions).

EXAMPLE 2

Expression of PLAP in E. coli

In order to express PLAP, the E. coli K12 strain RM82 (DSM 5445, a methionine revertant of ED 8654, (Murray, N. E. (1977), Molo Gen. Genet. 150, 53–61) was transformed with the PLAP expression plasmid pPLAP (ampicillin resistance) and the lacI repressor plasmid pUBS500 (kanamycine resistance; production and description see: EP-A 0 373 365).

The RM82/pUBS500/pPLAP cells were grown in DYT medium (1% (weight/volume) yeast extract, 1% (weight/volume) Bacto tryptone, Difco, and 0.5% NaCl) containing 50 mg/l ampicillin and 50 mg/l kanamycin up to an optical density of 0.6-0.9 at 550 nm and subsequently induced with IPTG (final concentration 1-5 mmol/l). After an induction phase of 4-8 hours the cells were harvested by centrifugation, washed with 25 mmol/l Tris-HCl buffer, pH 7.5 and stored at $-20°$ C. until further processing.

EXAMPLE 3

PLAP expression analysis in E. coli

The cell pellet from 1 ml centrifuged culture medium (RM82/pUBS500/pPLAP cells) was resuspended in 0.25 ml 10 mmol/l phosphate buffer, pH 6.8 and 1 mmol/l EDTA and the cells were lysed by ultrasonic treatment. After centrifugation 1/5 volumes 5×SDS sample buffer (1×SDS sample buffer: 50 mmol/l Tris-HCl, pH 6.8, 1% SDS, 1% mercaptoethanol, 10% glycerol, 0.001% bromophenol blue) was added to the supernatant. The insoluble cell debris fraction was resuspended in 0.3 ml 1×SDS sample buffer containing 6-8 mol/l urea, the samples were incubated for 5 minutes at 95° C. and centrifuged. Afterwards the proteins were separated by SDS polyacrylamide gel electrophoresis (PAGE) (Laemmli, U. K. (1970), Nature 227, 680–685) and stained with Coomassie Brilliant Blue R dye.

In addition the proteins which were separated electrophoretically were transferred onto nitrocellulose filters, fixed (Towbin, H. (1979), Proc. Natl., Acad. Sci. USA 76, 4350) and the PLAP immunoreactive proteins were detected using a specific anti-PLAP antiserum.

The PLAP protein synthesized in E. coli was homogeneous and was found exclusively in the insoluble cell debris fraction (IB's). No shortened PLAP fragments could be detected by means of SDS-PAGE and Western blot analysis. The proportion of PLAP to total IB protein was approximately 30–50%.

EXAMPLE 4

Preparation of PLAP-IBs 5 g (wet weight) E. coli RM82/pUBS500/pPLAP cells were homogenized in 25 ml 0.1 mol/l Tris-HCl, pH 7.0 at 4° C. using an Ultraturrax (10000 rpm). After addition of 7.5 mg lysozyme (1.5 mg lysozyme per gram cell material) and mixing for a short time with the Ultraturrax, the preparation was incubated for 30 minutes at 4° C. Afterwards the cells were completely lysed mechanically by means of highpressure dispersion. The DNA was digested for 30 minutes at 25° C. by addition of $MgCl_2$ (to a final. concentration of 2 mmol/l) and DNAse (to a final concentration of 1 mg/100 ml). Subsequently 0.5 parts by volume 60 mmol/l EDTA, 6% Triton X100, 1.5 mol/l NaCl, pH 7.0 was added to the lysed solution and incubated for a further 30 minutes at 4° C. Afterwards the insoluble components (cell debris and IBs) were sedimented by centrifugation using a Sorvall centrifuge (SS34/20000 rmp/10 min/4° C.). The pellet was resuspended in 40 ml 0.1 mol/l Tris-HCl, 20 mmol/l EDTA, pH 6.5 with an Ultraturrax and centrifuged again as above. The pellet of this centrifugation represented the PLAP-IBs.

Solubilization of recombinant PLAP 25 mg of the PLAP-IBs (wet weight) was suspended for at least 2 hours at room temperature in 3 of ml 0.1 mol/l Tris-HCl, 8 mol/l urea, pH 8.0 (RT) in the presence of 100 mmol/l DTE. Subsequently the pH value of the solubilization mixture was adjusted to 3.0–4.0 with HCl and insoluble components were removed by centrifugation. The reducing agent DTE was completely removed by dialysing the supernatant for 2×2 hours at room temperature, once overnight at 4° C. and again 1×2 hours at room temperature against 8 mol/l urea, 5 mmol/l HCl, pH ca. 4.0 (dialysis buffer ca. 500 ml each time). The protein concentration of the solubilization mixtures was ca. 2.5 mg/ml. Aliquots of the respective solubilization mixtures could be stored for at least two weeks at −70° C. if required.

EXAMPLE 5

Renaturation of alkaline phosphatase

The renaturation of alkaline phosphatase was started by a 1:200 dilution of the dialysed solubilization or denaturation mixture (see example 4) in renaturation buffer. The final concentration of alkaline phosphatase in the renaturation mixture was ≦10 μg/ml. All renaturation mixtures contained a mixture of reduced (GSH) and oxidized glutathione (GSSG) in order to facilitate the correct formation of disulphide bridges. If not stated otherwise the renaturation preparations were thermostated at 20° C.

PLAP obtained from examples 1 to 4 or a commercially available AP from calf intestine which had been pretreated according to Example 4, Solubilization, was used for the renaturation. Since essentially the same results were obtained with both enzymes, the results obtained using PLAP are stated in the following as representative.

Detection of renaturation

The renaturation of alkaline phosphatase was determined via its activity in a routine enzyme test in which the cleavage of p-nitrophenyl phosphate was monitored spectrometrically (Bretaudiere, J. -P. and Spillman, T. (1984), Methods of Enzymatic Analysis, VCH, 75–82).

EXAMPLE 6

Attempts to renature under standard conditions

It is not possible to renature AP when the proposals described in the literature (Rudolph, R. (1990), Modern Methods in Protein and Nucleic Acid Research, Walter de Gruyter, Berlin, N.Y., p. 149–171) are used as a guideline for the renaturation buffers (standard buffers see below).

| Standard buffer: | 0.1 mol/l | Tris-HCl/pH 8.0 |
|---|---|---|
| | 10 mmol/l | $MgCl_2$ |
| | 0.1 mmol/l | $ZnCl_2$ |
| | 5 mmol/l | GSH or 4 mmol/l GSH |
| | 1 mmol/l | GSSG or 2 mmol/l GSSG |

EXAMPLE 7

Renaturation by $Na_2SO_4$

Solubilized PLAP was diluted in renaturation buffer which contained increasing amounts of $Na_2SO_4$. As can be seen from Table 1, PLAP can be successfully renatured starting with a $Na_2SO_4$ concentration of 0.3 mol/l in the renaturation mixture and renaturation efficiency also increases with increasing $Na_2SO_4$ concentration.

| Renaturation buffer: | 0.1–0.6 mol/l | $Na_2SO_4$ |
|---|---|---|
| | 0.2 mol/l | Tris-HCl/pH 8.0 |
| | 10 mmol/l | $MgCl_2$ |
| | 0.1 mmol/l | $ZnCl_2$ |
| | 4 mmol/l | GSH |
| | 2 mmol/l | GSSG |
| | renaturation period: | 20 h or 40 h. |

EXAMPLE 8

Renaturation by $K_2SO_4$ or $(NH_4)_2SO_4$

Solubilized PLAP was diluted in renaturation buffer which contained increasing amounts of $K_2SO_4$ or $(NH_4)_2SO_4$. Both components enable an efficient renaturation of PLAP which is dependent on their concentration (see Table 2).

| Renaturation buffer: | 0–1.4 mol/l | $(NH_4)_2SO_4$ or |
|---|---|---|
| | 0–0.6 mol/l | $K_2SO_4$ |
| | 0.2 mol/l | Tris-HCl/pH 8.0 |
| | 10 mmol/l | $MgCl_2$ |
| | 0.1 mmol/l | $ZnCl_2$ |
| | 4 mmol/l | GSH |
| | 2 mmol/l | GSSG |
| | renaturation period: | approximately 90 h |

EXAMPLE 9

Renaturation by carbohydrates or polyalcohols

The presence of sugars or polyalcohols and related substances in the renaturation mixture enables PLAP to be renatured. The dependence of the renaturation efficiency on the concentration of the individual carbohydrates was examined systematically. These results are summarized in Table 3. From this it can be seen that there is an increase in renaturation efficiency in the presence of the examined substances galactose, glucose, fructose, lactose, maltose, sucrose, sorbitol, glycerol, ethylene glycol and arabinose. Furthermore an increased renaturation efficiency was found for erythritol and inositol (without a figure).

| Renaturation buffer: | 0–40% (w/v) | D(+) galactose D(+) glucose D(−) fructose, β-lactose, maltose monohydrate, sucrose, sorbitol, glycerol, ethylene glycol, or L(+) arabinose |
|---|---|---|
| | 0.2 mol/l | Tris-HCl/pH 8.0 |
| | 40 mmol/l | $MgCl_2$ |
| | 0.1 mmol/l | $ZnCl_2$ |
| | 4 mmol/l | GSH |
| | 4 mmol/l | GSSG |
| renaturation period: | about 40 h | |

EXAMPLE 10

Synergistic effect when combining carbohydrates or-/and polyalcohols with sulfate salts The combined effect of carbohydrates/polyalcohols and sulfate salts on renaturation efficiency is synergistic. The presence of one representative from each of the two classes of substances in the renaturation buffer results in a higher renaturation efficiency than that caused by each class of substances when used alone. These results are summarized in Table 4 for $K_2SO_4$ and glycerol.

| Renaturation buffer: | 0–30% (w/v) | glycerol in the presence of 0 mol/l, 0.09 mol/l and 0.18 mol/l $K_2SO_4$ |
|---|---|---|
| | 0.2 mol/l | Tris-HCl/pH 8.0 |
| | 40 mmol/l | $MgCl_2$ |
| | 0.1 mmol/l | $ZnCl_2$ |
| | 4 mmol/l | GSH |
| | 4 mmol/l | GSSG |
| renaturation period: | ca. 40 h | |

EXAMPLE 11

Variation of the pH value in the renaturation mixture

The results of a systematic variation of the pH value of the renaturation buffer are shown in Table 5. The optimal pH value for the renaturation is in the region of 8.0 for all the $Na_2SO_4$ concentrations tested (0.1 to 0.6 mol/l; data for 0.1 and 0.2 mol/l are not shown).

| Renaturation buffer: | 0.1–0.6 mol/l | $Na_2SO_4$ |
|---|---|---|
| | 0.2 mol/l | Tris-HCl, pH 7.25–8.5 |
| | 10 mmol/l | $MgCl_2$ |
| | 0.1 mmol/l | $ZnCl_2$ |
| | 4 mmol/l | GSH |
| | 4 mmol/l | GSSG |
| renaturation period: | ≧40 h | |

EXAMPLE 12

Variation of redox conditions in the renaturation mixture

The dependence of renaturation efficiency on the GSH or GSSG concentration in the renaturation buffer is shown in tables 6–8.

| Renaturation buffer: | 0.2 mol/l | Tris-HCl/pH 8.0 |
|---|---|---|
| | 10 mmol/l | $MgCl_2$ |
| | 0.1 mmol/l | $ZnCl_2$ |
| | 0.6 mol/l | $Na_2SO_4$ |
| renaturation period: | 20 h or 90 h | |

Table 6 shows the renaturation efficiency with varying GSH concentrations and a constant GSSG concentration (4 mmol/l GSSG). Table 7 shows the renaturation efficiency with varying GSSG concentrations and a constant GSH concentration (4 mmol/l GSH). Table 8 shows the renaturation efficiency with varying GSSG and GSH concentrations and equimolar amounts of GSH and GSSG in the renaturation buffer.

EXAMPLE 13

Variation of $ZnCl_2$ and $MgCl_2$ concentration in the renaturation mixture

As can be seen in Tables 9 and 10, the renaturation of PLAP is significantly improved by $Zn^{2+}$ ions (e.g. $ZnCl_2$) and $Mg^{2+}$ ions (e.g. $MgCl_2$).

Table 9 shows the renaturation efficiency when varying the $ZnCl_2$ concentration.

| Renaturation buffer: | 0–0.5 mmol/l | $ZnCl_2$ |
|---|---|---|
| | 0.2 mol/l | Tris-HCl/pH 8.0 |
| | 10 mmol/l | $MgCl_2$ |
| | 4 mmol/l | GSH |
| | 4 mmol/l | GSSG |
| | 0.6 mol/l | $Na_2SO_4$ |
| renaturation period: | 20 h or 90 h | |

Table 10 shows the renaturation efficiency when varying the $MgCl_2$ concentration

| Renaturation buffer: | 0–180 mmol/l | $MgCl_2$ |
|---|---|---|
| | 0.2 mol/l | Tris-HCl/pH 8.0 |
| | 0.1 mmol/l | $ZnCl_2$ |
| | 4 mmol/l | GSH |
| | 4 mmol/l | GSSG |
| | 0.6 mol/l | $Na_2SO_4$ |
| renaturation period: | 20 h or 90 h | |

EXAMPLE 14

Influence of temperature on the renaturation efficiency

The dependence of the renaturation efficiency on the renaturation temperature was examined for several of the identified folding activators. An efficient renaturation occurred in the whole range tested from 15° C. to 30° C. The results for some of the folding activators used are summarized in Table 11 ($Na_2SO_4$, $K_2SO_4$, $(NH_4)_2SO_4$, sorbitol and glycerol).

TABLE 1

Dependence of the renaturation efficiency on the Na$_2$SO$_4$ concentration and on the duration of renaturation.

| Concentration [mol/l] | Activity [ΔA/min × 1000] | |
|---|---|---|
| | 20 h | 40 h |
| 0,1 | 2 | 4 |
| 0,2 | 3 | 8 |
| 0,3 | 7 | 16 |
| 0,4 | 40 | 130 |
| 0,5 | 84 | 220 |
| 0,6 | 103 | 201 |

TABLE 2

Dependence of the renaturation efficiency on the K$_2$SO$_4$ or (NH$_4$)$_2$SO$_4$ concentration

| Concentration [mol/l] | Activity [ΔA/min × 1000] | |
|---|---|---|
| | (NH$_4$)$_2$SO$_4$ | K$_2$SO$_4$ |
| 0 | 1 | 1 |
| 0,1 | 2 | 2 |
| 0,2 | 2 | 8 |
| 0,3 | 2 | 25 |
| 0,4 | 4 | 94 |
| 0,5 | 8 | 87 |
| 0,6 | 12 | 67 |
| 0,7 | 19 | / |
| 0,8 | 13 | / |
| 0,9 | 8 | / |
| 1,0 | 2 | / |
| 1,1 | 1 | / |
| 1,2 | 1 | / |

TABLE 3

Dependence of the renaturation efficiency on the concentration of various carbohydrates and polyalcohols. Gal: D(+)-galactose, Glu: D(+)-glucose, Fru: D(−)-fructose, Lac: β-lactose, Mal: maltose, suc: sucrose, Sor: sorbitol, Gly: glycerol, Eth: ethylene glycol, Ara: L(+)-arabinose.

| [%] | Activity [ΔA/min × 1000] | | | | | | | | | |
|---|---|---|---|---|---|---|---|---|---|---|
| | Gal | Glu | Fru | Lac | Mal | Suc | Sor | Gly | Eth | Ara |
| 0 | 3 | 3 | 3 | 3 | 3 | 3 | 3 | 3 | 3 | 3 |
| 2 | 2 | / | / | / | / | / | / | / | / | / |
| 2,5 | / | / | / | / | / | / | / | / | / | / |
| 4 | 2 | 5 | 4 | 5 | 4 | 3 | 4 | 4 | 4 | 6 |
| 5 | / | / | / | / | / | / | / | / | / | / |
| 6 | 4 | / | / | / | / | / | / | / | / | / |
| 7,5 | / | / | / | / | / | / | / | / | / | / |
| 8 | 8 | 7 | 7 | 9 | 4 | 5 | 8 | 8 | 5 | 19 |
| 10 | 17 | / | / | / | / | / | / | 12 | / | / |
| 12 | 31 | 10 | 20 | 25 | 6 | 7 | 29 | 22 | 9 | 47 |
| 14 | / | / | / | / | / | / | / | 41 | / | / |
| 16 | 68 | 61 | 38 | 51 | 9 | 17 | 85 | 61 | 21 | 70 |
| 18 | / | / | / | / | / | / | / | 77 | / | / |
| 20 | 92 | 86 | 86 | / | 18 | 44 | 120 | 121 | 21 | 89 |
| 22 | / | / | / | / | / | / | / | 136 | / | / |
| 24 | / | 122 | 134 | / | 37 | 70 | 146 | 135 | 30 | 97 |
| 26 | / | / | / | / | / | / | / | 165 | / | / |
| 28 | / | / | / | / | / | / | / | 203 | / | / |
| 30 | / | / | / | / | / | / | / | 167 | / | / |
| 32 | / | 134 | 142 | / | 58 | 101 | 136 | 174 | 16 | 71 |
| 36 | / | / | / | / | / | / | / | 170 | / | / |
| 40 | / | 76 | 149 | / | 49 | 51 | 62 | 172 | 6 | 30 |

TABLE 4

Effect of glycerol and K$_2$SO$_4$ on the renaturation efficiency.

| Concentration glycerol [%] | Activity [ΔA/min × 1000] | | |
|---|---|---|---|
| | glycerol | glycerol + 0,09M K$_2$SO$_4$ | glycerol + 0,18M K$_2$SO$_4$ |
| 0 | 1 | 1 | 2 |
| 4,5 | 7 | 7 | 10 |
| 9 | 9 | 18 | 36 |
| 13,5 | 22 | 58 | 99 |
| 18 | 58 | 120 | 145 |
| 22,5 | 113 | 116 | 206 |
| 27 | 144 | 221 | 213 |
| 31,5 | 153 | 220 | 239 |

TABLE 5

Dependence of the renaturation efficiency on the pH value.

| pH value | Activity [ΔA/min × 1000] | | | |
|---|---|---|---|---|
| | 0,3M Na$_2$SO$_4$ | 0,4M Na$_2$SO$_4$ | 0,5M Na$_2$SO$_4$ | 0,6M Na$_2$SO$_4$ |
| 7,25 | 2 | 3 | 3 | 2 |
| 7,50 | 16 | 19 | 25 | 18 |
| 7,75 | 39 | 99 | 147 | 109 |
| 8,00 | 16 | 129 | 220 | 201 |
| 8,25 | 14 | 74 | 153 | 191 |
| 8,50 | 4 | 23 | 77 | 119 |

TABLE 6

Dependence of the renaturation efficiency on the GSH concentration. GSSG concentration: 4 mM.

| GSH [mM] | Activity [ΔA/min × 1000] | |
|---|---|---|
| | after 20 h | after 90 h |
| 0 | 0 | 9 |
| 1 | 21 | 41 |
| 2 | 35 | 76 |
| 3 | 31 | 88 |
| 4 | 12 | 85 |
| 5 | 3 | 51 |
| 6 | 1 | 59 |
| 7 | 1 | 46 |
| 8 | 1 | 45 |
| 9 | 1 | 62 |
| 10 | 1 | 41 |

TABLE 7

Dependence of the renaturation efficiency on
the GSSG concentration.
GSH concentration: 4 mM.

| GSSG [mM] | Activity [ΔA/min × 1000] | |
|---|---|---|
| | after 20 h | after 90 h |
| 0 | 0 | 9 |
| 1 | 2 | 39 |
| 2 | 5 | 50 |
| 3 | 8 | 53 |
| 4 | 13 | 87 |
| 5 | 15 | 74 |
| 6 | 12 | 74 |
| 7 | 15 | 96 |
| 8 | 14 | 92 |
| 9 | 14 | 99 |
| 10 | 15 | 89 |

TABLE 8

Dependence of the renaturation efficiency on
the GSH and GSSG concentration at an equimolar
ratio of GSH/GSSG.

| GSH & GSSG [mM] | Activity [ΔA/min × 1000] | |
|---|---|---|
| | 20 h | 90 h |
| 0,1 | 1 | 1 |
| 0,5 | 1 | 2 |
| 1,0 | 4 | 9 |
| 2,0 | 20 | 46 |
| 4,0 | 14 | 87 |

TABLE 9

Dependence of the renaturation efficiency on
the $ZnCl_2$ concentration.
$MgCl_2$ concentration: 10 mM.

| $ZnCl_2$ [mM] | Activity [ΔA/min × 1000] | |
|---|---|---|
| | 20 h | 90 h |
| 0,000 | 1 | 1 |
| 0,050 | 2 | 88 |
| 0,075 | 5 | 74 |
| 0,100 | 7 | 65 |
| 0,125 | 12 | 35 |
| 0,150 | 15 | 55 |
| 0,175 | 12 | 40 |

TABLE 9-continued

Dependence of the renaturation efficiency on
the $ZnCl_2$ concentration.
$MgCl_2$ concentration: 10 mM.

| $ZnCl_2$ [mM] | Activity [ΔA/min × 1000] | |
|---|---|---|
| | 20 h | 90 h |
| 0,200 | 11 | 38 |
| 0,250 | 10 | 25 |
| 0,300 | 7 | 16 |
| 0,500 | 2 | 4 |

TABLE 10

Dependence of the renaturation efficiency on
the $MgCl_2$ concentration.
$ZnCl_2$ concentration: 0.1 mM.

| $MgCl_2$ [mM] | Activity [ΔA/min × 1000] | |
|---|---|---|
| | 20 h | 90 h |
| 0 | 1 | 1 |
| 5 | 4 | 53 |
| 10 | 7 | 54 |
| 20 | 13 | 71 |
| 30 | 16 | 81 |
| 40 | 20 | 91 |
| 50 | 17 | 75 |
| 60 | 17 | 77 |
| 70 | 16 | 68 |
| 80 | 9 | 74 |
| 100 | 8 | 72 |
| 150 | 2 | 46 |
| 180 | 1 | 42 |

TABLE 11

Influence of temperature on the renaturation efficiency.

| Temperature [°C.] | Activity [ΔA/min × 1000] | | | | |
|---|---|---|---|---|---|
| | 0,6M $Na_2SO_4$ | 0,45M $K_2SO_4$ | 0,7M $(NH_4)_2SO_4$ | 25% glycerol | 25% Sorbitol |
| 16 | 30 | 37 | 5 | 70 | 62 |
| 18 | 43 | 78 | 9 | 109 | 141 |
| 20 | 72 | 127 | 31 | 162 | 219 |
| 22 | 82 | 124 | 43 | 207 | 239 |
| 24 | 85 | 132 | 20 | 203 | 247 |
| 26 | 66 | 84 | 25 | 227 | 253 |
| 28 | 63 | 72 | 23 | 202 | 233 |

We claim:

1. A process for the production of biologically active, eukaryotic alkaline phosphatase, comprising:
   a) expressing a DNA sequence coding for eukaryotic alkaline phosphatase in a prokaryotic host cell to produce eukaryotic alkaline phosphatase;
   b) lysing said prokaryotic host cell to obtain a lysate;
   c) isolating eukaryotic alkaline phosphatase from said lysate;
   d) solubilizing said isolated eukaryotic alkaline phosphatase under denaturing conditions in the presence of a reducing agent; and
   e) renaturing said isolated eukaryotic alkaline phosphatase in the presence of at least one stabilizing agent to obtain biologically active, eukaryotic alkaline phosphatase wherein said stabilizing agent is present in an amount effective to stabilize said eukaryotic alkaline phosphatase and is selected from the group consisting of a sulfate salt, carbohydrate, or polyalcohol having at least 2 or more carbon atoms.

2. The process of claim 1 wherein said stabilizing agent is selected from the group consisting of at least one sulfate salt, carbohydrate, or polyalcohol having at least 2 carbon atoms.

3. The process of claim 1, wherein said stabilizing agent is at least one sulfate salt.

4. The process of claim 1 wherein said sulfate salt is at least one of the sulfate salts selected from the group consisting of sodium sulfate, potassium sulfate, or ammonium sulfate.

5. The process of claim 4 wherein said sulfate salt is sodium sulfate.

6. The process of claim 4 wherein said sulfate salt is potassium sulfate.

7. The process of claim 4, wherein sodium sulfate is added in an amount of 0.3–1 mol/l, potassium sulfate is added in an amount of 0.1–0.6 mol/l, and ammonium sulfate is added in an amount of 0.3–1 mol/l.

8. The process of claim 2, wherein said stabilizing agent is at least one carbohydrate.

9. The process of claim 8, wherein said carbohydrate is at least one of the carbohydrates selected from the group consisting of a pentose, hexose, or disaccharide.

10. The process of claim 8, wherein the total amount of carbohydrate added is 5 to 50% weight/volume relative to the volume of the renaturation mixture.

11. The process of claim 2, wherein said stabilizing agent is at least one polyalcohol, said polyalcohol having at least 2 carbon atoms.

12. The process of claim 11 wherein said polyalcohol is at least one of the polyalcohols selected from the group consisting of sorbitol, glycerol, erythritol, inositol, ethylene glycol.

13. The process of claim 11, wherein the total amount of polyalcohol added is 5 to 50% weight/volume relative to the volume of the renaturation mixture.

14. The process of claim 1, wherein the renaturation step is done in the presence of a mixture of a sulfate salt, a carbohydrate, and a polyalcohol having at least two carbon atoms.

15. The process of claim 1, wherein the renaturation step is done in the presence of a mixture of a sulfate salt and a polyalcohol having at least two carbon atoms.

16. The process of claim 1, wherein the renaturation step is done in the presence of a mixture of a carbohydrate and a polyalcohol having at least two carbon atoms.

17. The process of claim 1, wherein the renaturation step is done in the presence of a mixture of a sulfate salt and a carbohydrate.

18. The process of claim 17, wherein said sulfate salt is sodium sulfate and said carbohydrate is glycerol.

19. The process of claim 1, wherein the renaturation step is carried out in the presence of zinc ions and magnesium ions.

20. The process of claim 1, wherein the renaturation step is carried out in the presence of sulfhydryl reagents.

21. The process of claim 1, wherein the renaturation step is carried out in a pH range of 6 to 10.

22. The process of claim 1, wherein said prokaryotic host cell is gram negative.

23. The process of claim 22, wherein said prokaryotic host cell is *E. coli*.

24. The process of claim 1, wherein the DNA sequence coding for said eukaryotic alkaline phosphatase is introduced into said host cell by transformation with a vector which contains at least one copy of said DNA sequence.

25. The process of claim 24, wherein said vector is plasmid pPLAP (DSM 7094).

26. Biologically active, eukaryotic alkaline phosphatase obtained by the process of claim 1.

* * * * *

UNITED STATES PATENT AND TRADEMARK OFFICE
CERTIFICATE OF CORRECTION

PATENT NO. : 5,434,067
DATED : July 18, 1995
INVENTOR(S) : Michaelis et al.

It is certified that error appears in the above-indentified patent and that said Letters Patent is hereby corrected as shown below:

| Column | Line | |
|---|---|---|
| 12 | 31 | Table 6, Col. 12, lines 25-69 is discontinuous. Col. 12, lines 58-68 should be lines 32-43. |
| 12 | 58 | Patent should read "1" not "0" in col. 2 of the table. |
| 12 | 58 | Patent should read "2" not "9" in col. 3 of the table. |

Signed and Sealed this

Seventeenth Day of June, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1:

```
GCGCGTCGAC  TCATGATCAT  CCCAGTTGAG  GAG                    33
```

( 2 ) INFORMATION FOR SEQ ID NO: 2:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 2:

```
                CATCCCATCG CCCAGG                                   16
```

( 2 ) INFORMATION FOR SEQ ID NO: 3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
                CAATTAAGCT TTTATCAGTC GGTGGTGCCG                    30
```